US011341832B2

(12) United States Patent
Eavis et al.

(10) Patent No.: US 11,341,832 B2
(45) Date of Patent: May 24, 2022

(54) FALL PREVENTION DEVICE

(71) Applicant: Peak Medtek Limited, Hope Valley (GB)

(72) Inventors: Robert Edward Charles Eavis, Buxton (GB); Thomas Julian Adler, Hope Valley (GB)

(73) Assignee: PEAK MEDTEK LIMITED, Hope Valley (GB)

( * ) Notice: Subject to any disclaimer, the term of this patent is extended or adjusted under 35 U.S.C. 154(b) by 0 days.

(21) Appl. No.: 16/893,320

(22) Filed: Jun. 4, 2020

(65) Prior Publication Data

US 2020/0388133 A1   Dec. 10, 2020

(30) Foreign Application Priority Data

Jun. 5, 2019 (GB) ..................... 1907985

(51) Int. Cl.
| | | |
|---|---|---|
| G08B 21/04 | (2006.01) | |
| A61B 5/11 | (2006.01) | |
| G08B 5/36 | (2006.01) | |
| A61B 5/00 | (2006.01) | |

(52) U.S. Cl.
CPC .......... *G08B 21/043* (2013.01); *A61B 5/1114* (2013.01); *A61B 5/1115* (2013.01); *A61B 5/1117* (2013.01); *A61B 5/4809* (2013.01); *A61B 5/7405* (2013.01); *A61B 5/746* (2013.01); *G08B 5/36* (2013.01); *G08B 21/0469* (2013.01)

(58) Field of Classification Search
CPC combination set(s) only.
See application file for complete search history.

(56) References Cited

U.S. PATENT DOCUMENTS

| | | | | |
|---|---|---|---|---|
| 2012/0233644 A1* | 9/2012 | Rao | ................... | H04M 1/72412 |
| | | | | 725/62 |
| 2013/0174252 A1* | 7/2013 | Weber | ................... | H04W 12/50 |
| | | | | 726/20 |
| 2015/0054639 A1* | 2/2015 | Rosen | ................. | H04M 3/2281 |
| | | | | 340/439 |

(Continued)

FOREIGN PATENT DOCUMENTS

| | | |
|---|---|---|
| JP | 2005185493 | 7/2005 |
| WO | 201707034 | 4/2017 |
| WO | 2018235628 | 12/2018 |

OTHER PUBLICATIONS

"What Is Your Circadina Rhythm and Why Is It Important?", Mar. 13, 2019, Integris, pp. 1-2. (Year: 2019).*

*Primary Examiner* — Nabil H Syed
*Assistant Examiner* — Cal J Eustaquio
(74) *Attorney, Agent, or Firm* — Quarles & Brady LLP (57) ABSTRACT

A fall prevention device comprising at least one sensor operable to detect a user has woken up while they are still within a bed and a notification unit operable to output a fall prevention warning to a user in response to the detection. By detecting when a user wakes up, rather than when they physically get out of bed, the device allows a fall prevention warning to be provided in advance of the user getting up. This warning can relate to a variety of different things (for example, warning the user to take their time before getting up, or to use the necessary aids), all in aid of reducing the likelihood of the user falling when they get up. The device thereby reduces the chances of a fall.

18 Claims, 4 Drawing Sheets

(56) References Cited

U.S. PATENT DOCUMENTS

2017/0098365 A1    4/2017  Takeishi
2018/0125256 A1*   5/2018  Tsern .................. A47C 27/082
2018/0233018 A1*   8/2018  Burwinkel ......... G08B 21/0492

* cited by examiner

Figure 4

FALL PREVENTION DEVICE

TECHNICAL FIELD OF THE INVENTION

The present invention relates to a fall prevention device, method of preventing falls and a system of preventing falls.

BACKGROUND TO THE INVENTION

Individuals suffering falls are one of the biggest causes of hospitalisations. Falls are particularly common for more vulnerable people (for example, older people) due to infirmities. Said vulnerable people are also more likely to need to be hospitalised by falls, since when they fall it is more likely the result will be a serious injury.

One of the most likely times for falls to occur is when a person is getting out of bed, since a person will have just woken up and so can, for example, be disorientated, dehydrated, lack vision aids, lack hearing aids and/or lack mobility aids such as walking sticks or frames.

Known systems, for example the system disclosed in US 2014/0221876 A1, monitor residents of care homes or other such facilities. Said systems use pressure pads (in particular, pressure pads in beds) to monitor the position of a resident, and notify a nurse or other trained medical professional when a change in the pressure pad is detected. These systems help to reduce the time between a fall occurring (which would be detected by the change in the pressure on the pad in a resident's bed) and a trained medical professional reaching the resident to treat any injury. However, the system cannot help prevent the falls in the first place, and so prevent an injury and resulting hospitalisation. The pressure pads only detect when a resident has got up from the bed, by which point a fall has either already occurred or is occurring.

In addition, the known systems are primarily designed for use in residential care homes or other places where trained medical professionals are on call. They are of less use in a user's home, given the reliance and summoning help (which may not be present in the home).

The object of the present invention is to eliminate or at least mitigate the problems discussed above.

SUMMARY OF THE INVENTION

According to a first aspect of the present invention, there is provided a fall prevention device comprising at least one sensor operable to detect a user has woken up while they are still within a bed and a notification unit operable to output a fall prevention warning to the user in response to the detection.

By detecting when a user has woken up while they are still within a bed, rather than when they physically get out of bed, the device allows a fall prevention warning to be provided in advance of the user getting up. This warning can relate to a variety of different things (for example, warning the user to take their time before getting up, or to use the necessary aids), all in aid of reducing the likelihood of the user falling when they get up. The device thereby reduces the chances of a fall.

In addition, by outputting the warning to the user no help is required to prevent a fall. This means the device is of more use in a user's home, and so helps to keep vulnerable and/or infirm users living independently.

The fall prevention device may comprise a plurality of sensors.

The or each sensor may be operable to detect a change in a characteristic of an environment, compare the detected change to a set threshold or respective set threshold for the characteristic, and determine whether the detected change indicates the user has woken up based on the comparison. The environment may be the detection angle of the or each sensor. The or each sensor may be operable to detect the magnitude of the change, compare the detected magnitude to a set change in the magnitude of characteristic, and determine the detected change indicates the user has woken up when the detected magnitude exceeds the set magnitude. The or each sensor may be operable to detect the resulting value of the characteristic after the change, compare the detected resulting value to a set value and determine the detected change indicates the user has woken up when the detected resulting value exceeds the set value. The or each sensor may be operable to detect the distance between the position of the change and the or each sensor, compare the detected distance to a set distance and determine the detected change is indicates the user has woken up when the detected distance is below the set distance.

The sensor or at least one of the sensors may be a light sensor operable to detect a change in light intensity in the environment. By being a light sensor, the sensor can detect when a user turns a light source on, such as a bedside light. Given this is often the first thing a user will do as they wake, this event can be used as an indication the user is waking up.

The sensor or at least one of the sensors may be a motion sensor operable to detect motion of the user. The sensor or at least one of the sensors may be an infrared sensor. The sensor or at least one of the sensors may be a laser break beam sensor. Detecting motion can be an alternative way of detecting a user is awaking, since a user will reach out to turn on a light source and the motion sensor can detect the movement of the arm.

The sensor or at least one of the sensors may be a proximity sensor operable to detect the presence of a user.

The sensor or at least one of the sensors may be a heart-rate monitor operable to detect a change in the user's heart-rate. The sensor or at least one of the sensors may be a blood pressure monitor operable to detect a change in the user's blood pressure. The heart-rate and/or blood pressure monitor may comprise an adhesive surface operable to stick to the user and keep the monitor in place on the user. Upon awakening, a user's heart-rate and blood pressure will change. This being the case, either can be used as an event indicating a user is awaking.

The fall prevention device may comprise a mobile device, wherein the notification unit forms part of the mobile device. In particular, the mobile device may be a mobile phone. The device comprising a mobile device allows it to be moved to different positions by different users, such that the device can be optimised for each user. It also allows it to be moved as a user moves and/or used in a variety of different places (for example, from a home to a hotel, care home and/or hospital).

The fall prevention device may be a handheld device. This results in the device taking up less space and allows the device to be placed upon a bedside table (where the first light a user turns on is typically positioned).

The fall prevention device may comprise a light apparatus. The light apparatus may be a bedside light. The light apparatus may be a lamp.

The presence of a light apparatus allows the fall prevention device to be integrated into or at least around a standard object in a bedroom, so an additional object in the room for fall prevention is not needed (thereby reducing clutter).

The fall prevention device may comprise a connection between the sensor or at least one of the sensors and the light apparatus, wherein the light apparatus is operable to generate a signal along the connection when the light apparatus turns on and the sensor is operable to detect the generated signal as the event. The connection may be a wired connection. The connection may be a wireless connection. The light apparatus may comprise a switch operable by a user to turn on the light apparatus, wherein the connection is between the sensor and the switch and the switch is operable to generate the signal along the connection.

By connecting the sensor and light apparatus and detecting the light turning on as the event, the fall prevention device can be fully integrated into the light apparatus. It is also typically cheaper and easier to make, since the required sensor is cheaper and easier to set up.

The notification unit may comprise a light source operable to output light as part of the fall prevention warning. The light source may be an LED. The light source may be a screen. The light source may be a touch screen. The light source may be configurable by the user so as to set the light intensity, repeating pattern and/or wavelengths. Outputting light can help to orientate and/or fully awaken a user. It is also particularly useful when the user in question suffers from hearing loss.

The notification unit may comprise a transmitter operable to output a signal to turn on a light source as part of the fall prevention warning. The transmitter allows the fall prevention device to turn on a light within the room, such as a lamp and/or room light.

When the fall prevention device comprises a light apparatus, the light apparatus may comprise a receiver operable to receive the outputted signal from the transmitter and a switch operable to turn the light apparatus on in response to the receiver receiving the outputted signal. This allows the fall prevention device to turn on the light apparatus into which it is integrated for the user.

The notification unit may comprise a speaker operable to output audio as part of the fall prevention warning. The speaker may be operable to output a verbal communication as part of the fall prevention warning. Using a verbal communication allows the fall prevention warning to be more specific, increasing the chances of it working.

The fall prevention device may comprise a microphone operable to record audio for use as part of the fall prevention warning. The microphone may be operable to record one or more verbal communications. The fall prevention device may comprise a receiver operable to receive audio recordings, for use as part of the fall prevention warning, from an external device. The receiver may be operable to receive verbal communication recordings, for use as part of the fall prevention warning. The receiver may be operable to receive audio recordings from a server, or from a direct wife or Bluetooth connection with another device.

The use of a microphone and/or a receiver allows verbal communications or other audio to be recorded and used as part of the fall prevention warning. The audio and/or verbal communication can thereby be tailored to the particular user. For example, the verbal communication can be by a family member, a friend, a carer, or a medical professional known to the user. By using the receiver, the audio can be changed and updated from a location remote to the fall prevention device.

The notification unit may comprise an induction loop operable to output instructions to a hearing aid, instructing a hearing aid to output audio, as part of the fall prevention warning. The transmitter allows a user with hearing loss to still hear a fall prevention warning.

The fall prevention unit may comprise an input unit operable to receive an input from a user.

The notification unit may be operable to stop outputting the fall prevention warning in response to the or each sensor no longer detecting the event. The input unit may be operable to turn the fall prevention warning off in response to a received input. The input unit may be operable to turn the fall prevention unit off in response to a received input. This prevents the fall prevention warning from going on overly long and thereby irritating the user, which would likely decrease the chances of them using it again.

The input unit may be operable to turn the fall prevention device on in response to a received input. The input unit may comprise one or more buttons. The input unit may comprise a physical switch. The input unit may comprise a touchscreen.

The fall prevention device may comprise a controller operable to monitor the time of day and control the notification unit so that it can only output the fall prevention warning to a user in response to the detection at certain times of the day. This reduces the chances of the fall prevention device going off when it is not required, for example in the middle of the night or day.

The notification unit may be operable to choose one of a plurality of fall prevention warnings to output. The notification unit may be operable to choose one of a plurality of fall prevention warnings to output randomly. The notification unit may be operable to choose one of a plurality of fall prevention warnings to output based on a set of criteria. The set of criteria may be any of the following: time of day, time since last fall preventing warning outputted, and/or details of the detection.

The input unit may be operable to receive a calibration input from a user. The fall prevention device may comprise a processor operable, in response to the input unit receiving the calibration input, to record the next change detected by the sensor or at least one of the sensors and set the detected change as the set threshold or respective threshold. This allows the device to be calibrated to the user's room, for example the light source in the room at the time the device is to output a warning, the specific motion the user plans to make and/or the user's heart-rate and/or blood pressure. This mitigates the chances of the fall prevention warning being outputted when it is not required.

The fall prevention device may comprise a battery operable to supply the fall prevention device with power. The fall prevention device may comprise an electrical connection operable to connect to an external power supply and supply power from the external power supply to the fall prevention device.

The fall prevention warning may comprise a repeating light and/or audio. The notification unit may be operable to output a plurality of fall prevention warnings, consecutively. The notification unit may be operable to output a checking message after the fall prevention warning or warnings.

When the fall prevention device comprises an input unit, the fall prevention device may additionally comprise an alarm transmitter operable to automatically output an alarm signal to an external device if no input is received at the input unit a set time after the checking message. The external device may be part of a dedicated health monitoring system and/or the emergency services. The alarm transmitter may be a telephone, wherein the alarm signal is a telephone call and the external device may be the phone of a set person. The alarm transmitter may be connected to a server, wherein the alarm signal is an online notification and the external device may be the online device of a set person. The set person may be any of the following: a family member, friend, a carer, a health professional, or the emergency services.

The fall prevention device may comprise a recorder operable to record the number of times a user wakes over a set period of time. The set period of time may be a course of a night. The recorder may be operable to record the number of times a user wakes over a set period by recording the number of times the or each sensor detects a user has woken up over the set time period. The recorded data may be stored on a memory drive. The memory drive may be a removable data drive. The recorder may be operable to transmit the recorded data at the end of the set period of time to an external device. The external device may be a server.

The fall prevention device may comprise a body wherein the or each sensor and notification unit form part of the body. By the or each sensor and notification unit forming part of the same body, the fall prevention device can be a self-contained device which is relatively easy to set up and use. The input unit, processor, controller, alarm transmitter, recorder and/or receiver may form part of the body. The body may be the mobile device. The body may be the handheld device. The body may be the mobile phone.

The fall prevention device may comprise a case forming an outer surface of the body. The case may be semi-transparent.

According to a second aspect of the present invention there is provided a method of preventing falls including providing a fall prevention device according to the first aspect, detecting a user has woken up while they are still within a bed using the or each sensor and outputting a fall prevention warning to the user via the notification unit in response to the detection.

The fall prevention device of the second aspect may comprise any combination or all of the optional features of the first aspect, as desired or appropriate.

According to a third aspect of the present invention there is provided a system of preventing falls comprising a fall prevention device according to the first aspect when it comprises a receiver operable to receive audio recordings, for use as part of the fall prevention warning, from an external device and the external device comprising a server operable to send recorded audio to the fall prevention device.

The fall prevention device of the third aspect may comprise any combination or all of the optional features of the first aspect, as desired or appropriate.

DETAILED DESCRIPTION OF THE INVENTION

In order that the invention may be more clearly understood one or more embodiments thereof will now be described, by way of example only, with reference to the accompanying drawings, of which.

Figure 1:
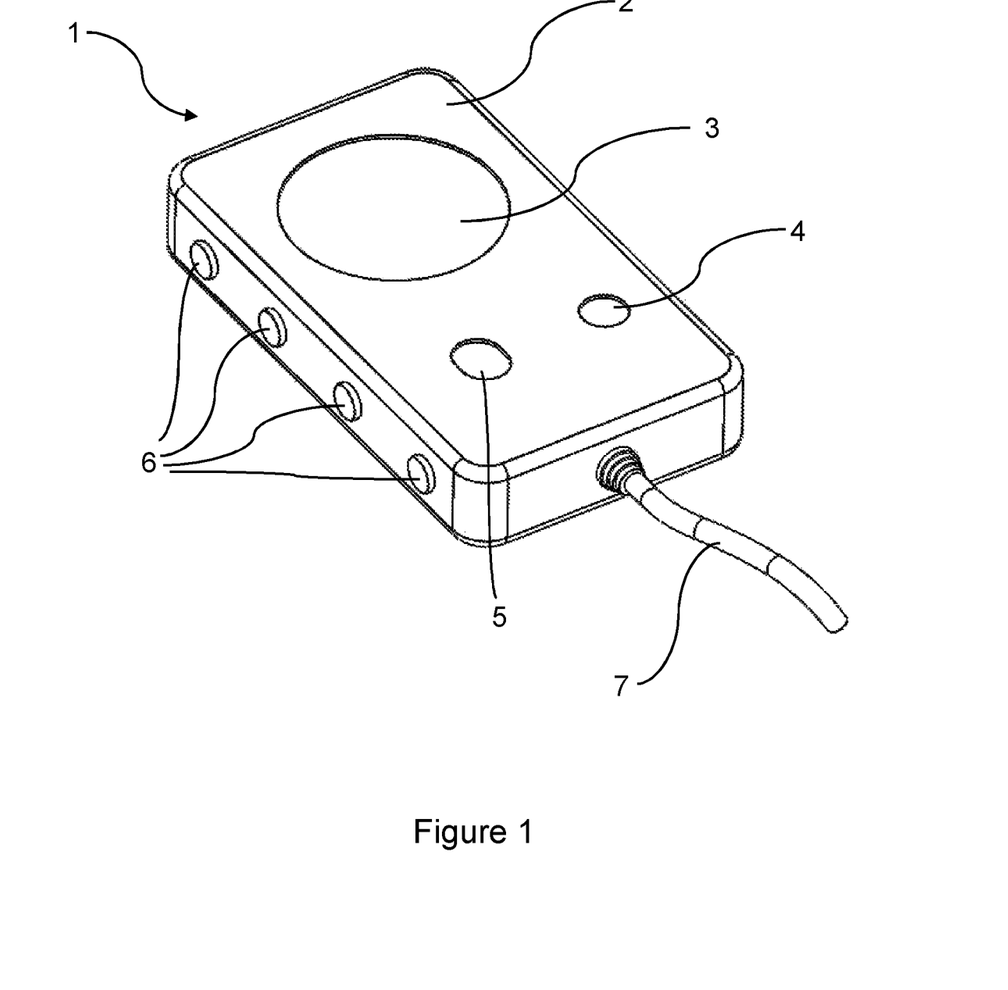
FIG. 1 shows a fall prevention device according to the present invention.
Figure 2:
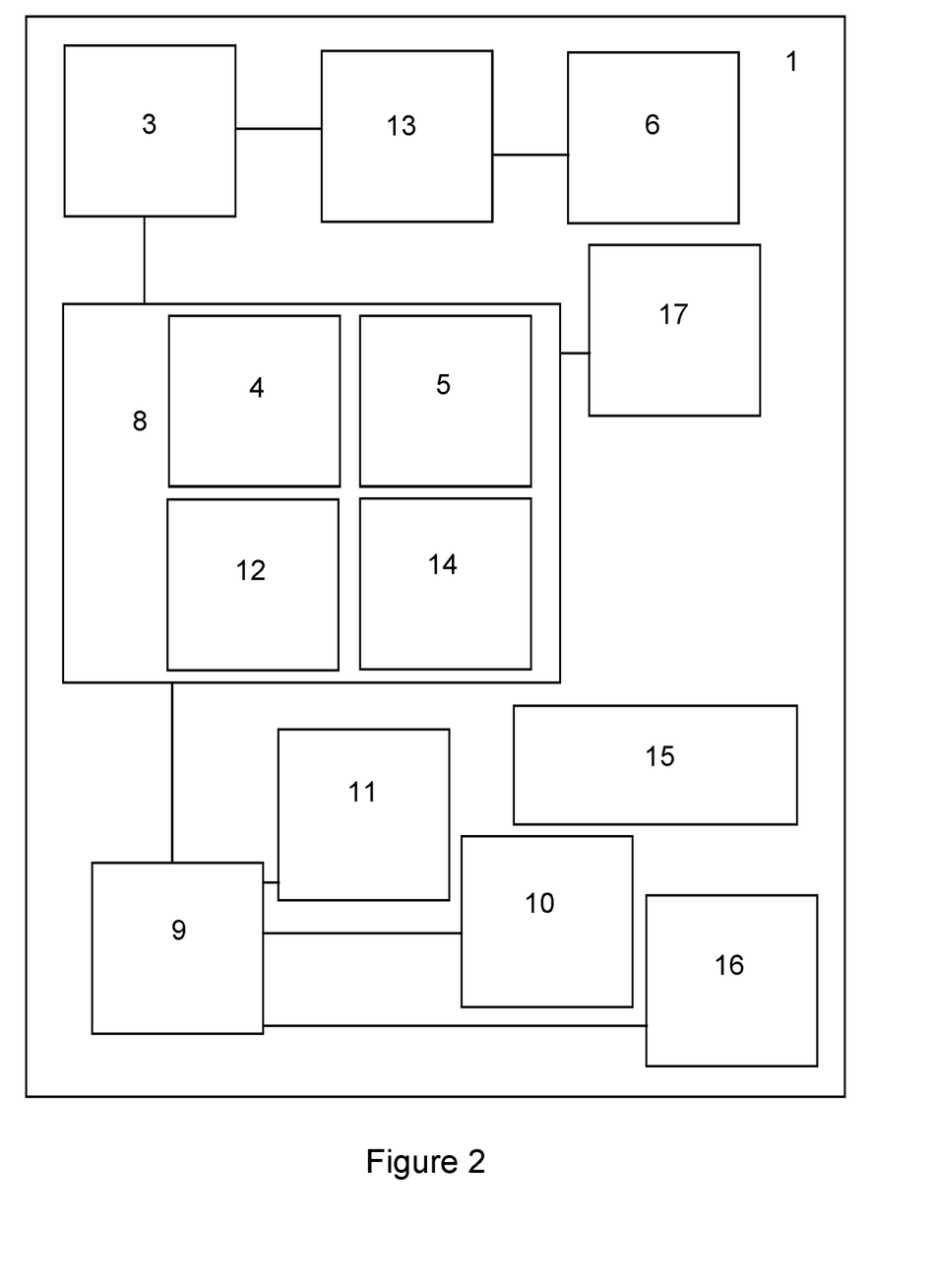
FIG. 2 shows a block diagram of the fall prevention device of FIG. 1.

As shown in FIGS. 1 and 2, the fall prevention device 1 is a mobile device comprising a body 2. The body 2 is a rectangular cuboid, with two surfaces and four, relatively short in comparison, sides extending between the edges of the surfaces. The corners where sides connect are rounded off. The outer surface of the body 2 consists of a case 19, which is semi-transparent.

The fall prevention device 1 comprises two sensors: a light sensor 3 and a motion sensor 18. The body 2 has a circular aperture within its front surface, through which the light sensor 3 can detect changes within the environment. The body 2 has a similar aperture for the motion sensor 18, although in this case the aperture is an elongate circle. The sensors 3, 18 are operable detect a user has woken up while they are still within a bed. While in this embodiment a light sensor 3 and a motion sensor 18 are used, the sensors 3, 18 can be one or more of a variety of other types of sensors: for example, a proximity sensor operable to detect the presence of a user, a heart-rate monitor operable to detect a user's heart rate and/or a blood pressure monitor operable to detect a user's blood pressure.

The fall prevention device 1 also comprises a speaker 4. The front surface of the body 2 comprises further circular aperture, much larger than the aperture for the light sensor, through which the speaker 4 is exposed to the environment.

The fall prevention device 1 comprises an LED 5, which is housed within the case 19. The speaker is operable to output audio, in particular verbal communications (either recorded or electronically generated) while the LED is operable to output light. Both do so as part of a fall prevention warning outputted by the fall prevention device 1. The audio and light outputted can be a single output, a repeating series and/or any pattern of outputs, as required for the user. Since the case 19 is semi-transparent, the light outputted by the LED 5 can pass through the case 19 and into the environment.

Out of a long side of the body 2 extends four buttons 6. These buttons 6 allow the fall prevention device 1 to receive inputs from the user.

A wire 7 extends from the bottom short side of the body. This wire 7 connects the fall prevention device 1 to an external power supply, and thereby provides power to the device 1. The fall prevention device 1 also comprises a battery 15, which provides power if the external power supply is disrupted or otherwise unavailable.

In use, the sensors 3, 18 will detect an event indicating a user is waking up. They do so by detecting a change in the environment within their respective detection angles. The sensors 3, 18 will then compare this detected change to a set threshold for the characteristic, and determined based on the comparison whether the detected change is an event indicating the user is waking up.

For the motion sensor 18, the detected change will be motion across and/or in the detection range of the sensor 18. The sensor 18 will compare the either the amount of motion detected and/or the distance of the position of the motion from the sensor 18 to respective set thresholds (of amount of motion and distance, respectively). If the amount of motion detected exceeds the respective set threshold and/or the distance detected is below the respective set threshold, the sensor 18 will consider the detected motion indicates the user has woken up. The motion sensor 18 is a infra-red sensor, operable to emit infra-red waves, receive the returning waves and determine whether there has been motion based on the comparison of the emitted an received waves.

For the light sensor 3, the detected change will be an increase in light intensity within the detection range. The sensor 3 will compare the resulting light intensity detected to a threshold of light intensity. If the detected light intensity exceeds the threshold, the sensor 3 will consider the detected change to indicate the user has woken up.

When a sensor 3, 18 is a proximity sensor, the detected change will be the presence of an object within the viewing range of the sensor 3, 18. The sensor 3, 18 will compare the distance of the object to the sensor to a set distance, and if the detected distance is below the set distance the sensor 3, 18 will determine the user has woken up.

When a sensor 3, 18 is a heart-rate or blood pressure monitor. In such cases, the sensor 3, 18 will be external to the body 2, and comprise an adhesive surface via which is can be attached to a user. The fall prevention device 1 will comprise a connection (either a wired or wireless connection) between the sensor 3, 18 and the body 2, to supply power to the sensor 3, 18 and for the sensor 3, 18 to send data back to the body 2.

Once at least one of the sensors 3, 18 detects a user has woken up, a notification unit 8 (of which the speaker 4 and LED 5 form part) of the fall prevention device 1 will output a fall prevention warning in response to the detection.

The fall prevention device 1 comprises a memory unit 9 and a microphone 10. The microphone allows audio (such as verbal communications) to be recorded on the fall prevention device 1, the recorded audio being stored on the memory unit 9. The fall prevention device 1 can then use the recorded audio as part of the fall prevention warning. This allows family, friends and/or medical professionals to record audio and so tailor the fall prevention warning to the user.

The fall prevention device 1 also comprises a receiver 11 operable to receive recorded audio from an external device (such as a server). The recorded audio can then be stored on the memory unit 9, and used by the fall prevention device 1 as part of the fall prevention warning. This allows family, friends and/or medical professionals to record audio (e.g. verbal communications) at a remote location to the fall prevention device 1.

The device 1 and server can together form part of a fall prevention system. The server can manage the device 1, including sending recorded audio for use as part of the fall prevention warning.

The notification unit 8 also comprises an induction loop 12, via which the notification unit 8 can output instructions (as part of the fall prevention warning) to a user's hearing aid to output audio. The audio instructed to output matches the audio outputted by the speaker 4.

Upon the sensor 3, 18 which detected the change no longer detecting the change, the notification unit 8 will stop outputting the fall prevention warning. Alternatively, the user can press a specific button 6. Upon receiving the input of the button press the notification unit 8 will stop outputting the fall prevention warning.

The fall prevention device 1 also comprises a processor 13. Upon the user pressing a particular button 6 for calibrating the fall prevention device 1, the processor 13 will record the next detected change at one of the sensor 3, 18 and set it as the respective set threshold. This allows a user to calibrate the device 1.

The notification unit also comprises a transmitter 14. As part of the fall prevention warning, the notification unit can transmit a signal via the transmitter 14 to turn on a light apparatus.

The fall prevention device 1 comprises a recorder 16. This recorder 16 can record the number of times the sensors 3, 18 detect a user has woken up in a set time period (for example, over one night). The recorder 16 can then store this recorded data on the memory unit 9. In addition, the recorder 16 can transmit the recorded data to an external device, such as the server in the case of the system. This recorded data can be used to monitor a user's sleeping patterns.

The memory unit 9 can store a plurality of fall prevention warnings, each of which can be made up of any combination of audio, light and/or signals to turn on external light sources. The notification unit 8 can then choose the fall prevention warning to use, either randomly or based on set criteria (such as time of day and/or details of the detection), depending upon how it has been set up. The notification unit 8 can also use multiple fall prevention warning, one after another.

A user pressing one of the buttons 6 of the fall prevention unit 1 indicates the user is ok. If the notification unit 8 does not receive this input signal a set time after outputting a fall prevention warning, the notification unit 8 will output an alarm signal to an external device. This external device can form part of a health monitoring system, the emergency services and/or be a phone of a family member, friend and/or medical professional.

The fall prevention device 1 comprises a controller 17. This controller 17 monitors the time of day and controls the notification unit so that it can only output the fall prevention warning to a user in response to the detection at certain times of the day. The certain times of day can be chosen by the user, by setting up the fall prevention device 1 and therefore the controller 17. This prevents fall prevention warnings from going off unnecessarily, for example when the user has not been asleep.

Figure 3:
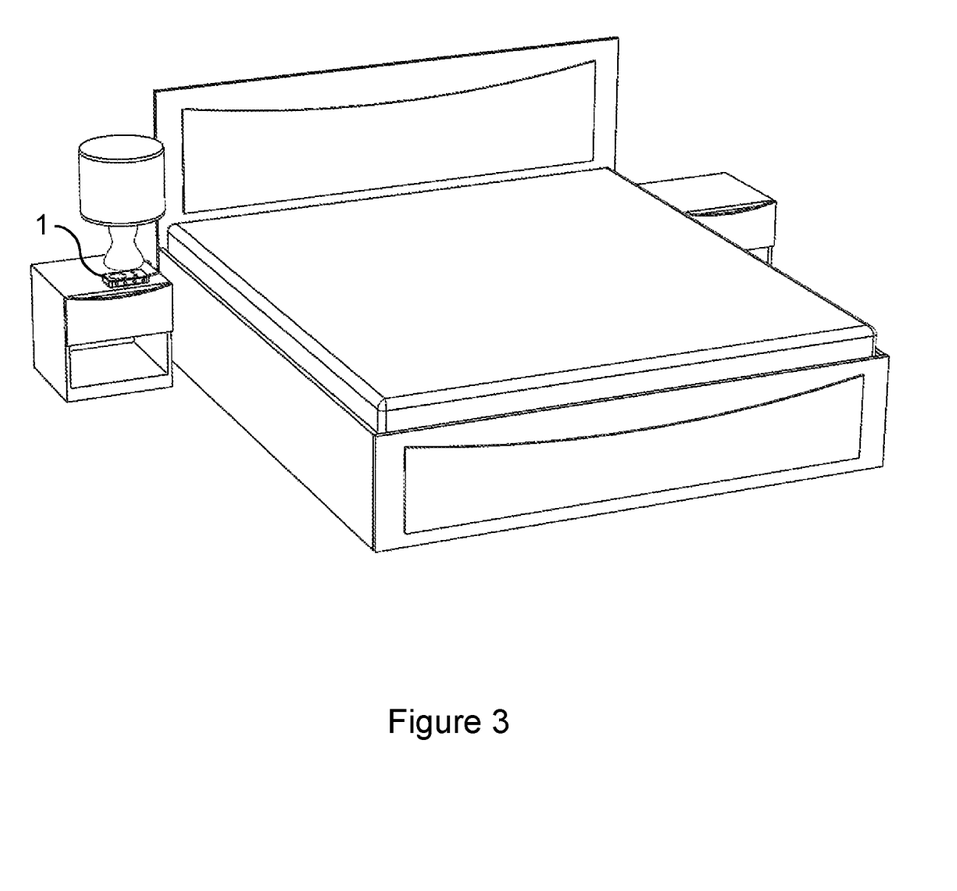
FIG. 3 shows the fall prevention device of FIG. 1 in use in a bedside setting.
Figure 4:
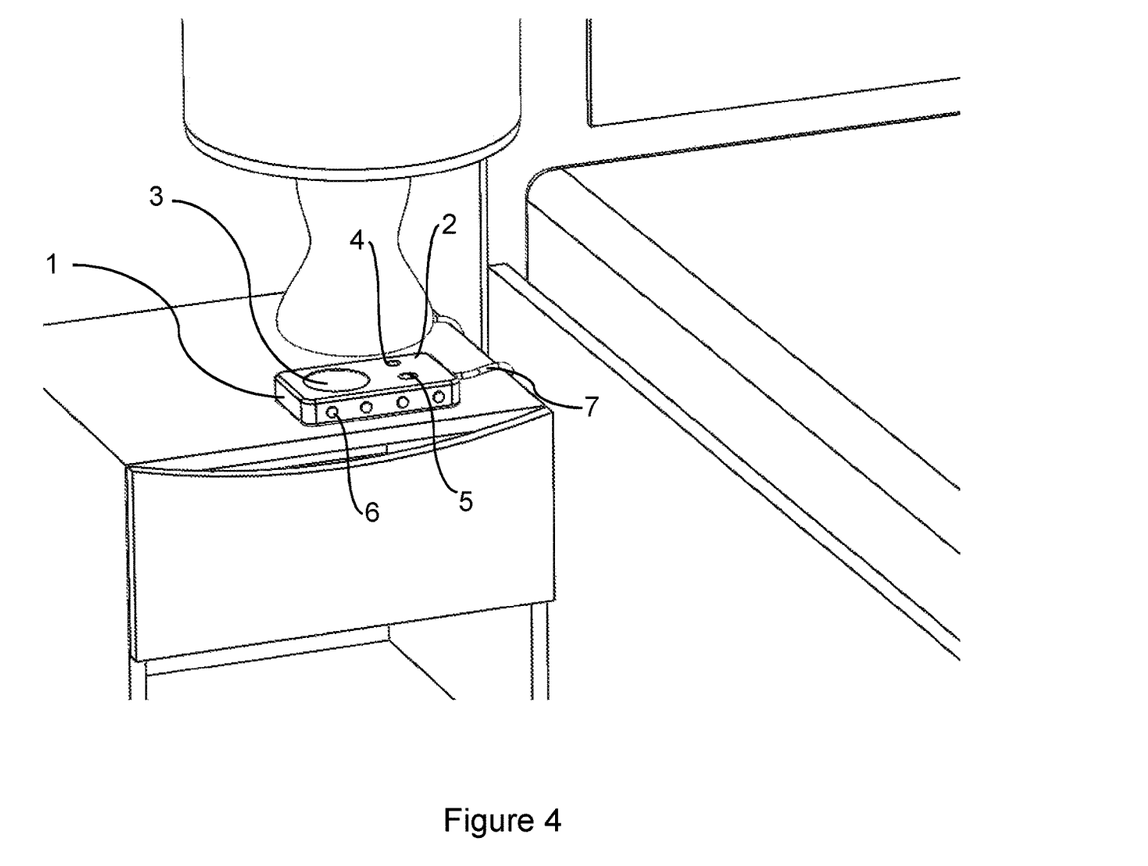
FIG. 4 shows a close up, focused on the fall prevention device, of FIG. 2.

As shown in FIGS. 3 and 4, in use the fall prevention device 1 is placed on a bedside next to a user in bed. The fall prevention device 1 will be plugged into a mains connection, so as to power it. The motion sensor 18 (or a proximity sensor, when one of the sensors 3, 18 is a proximity sensor) will detect when a user reaches across the bedside (and therefore the device 1) to turn on the bedside light. The light sensor 3 will detect when a user turns on the bedside light. In each case, the sensors 3, 18 will therefore detect a user has woken up while they are still within the bed.

When a sensor 3 is a heart-rate and/or blood pressure monitor, the monitor will be attached to a user when they enter the bed to sleep. Upon waking a user's heart-rate and blood pressure will change, and the monitor will therefore detect the user is awake.

In an alternative embodiment, the fall prevention device 1 can be integrated into the bedside light. In such cases, another option for a sensor 3, 18 is to be connected to the switch of the bedside light which turns the light on. Upon the light being turned on via the switch, the switch will generate a signal upon the connection which the sensor 3, 18 will detect. The sensor 3, 18 will thereby detect a user has woken up.

In another alternative embodiment, the fall prevention device 1 can be a mobile device. In such cases, the hardware of the mobile device can be used as the hardware required for the fall prevention device 1, with the hardware being run as required by a software application downloaded on the mobile device.

The one or more embodiments are described above by way of example only.

Many variations are possible without departing from the scope of protection afforded by the appended claims.

The invention claimed is:

1. A fall prevention device comprising one or more sensors, one or more of the sensors being operable to detect a user is awake while they are still within a bed and a notification unit operable to output a fall prevention warning to the user in response to the detection; wherein at least one of the sensors is a light sensor operable to detect a change in the light intensity of an environment, compare the detected change to a set threshold or respective set threshold for light intensity, and determine whether the detected change indicates the user is awake based on the comparison, wherein the notification unit is operable to choose one of a plurality of fall prevention warnings to output randomly.

2. A fall prevention device according to claim 1 wherein at least one of the sensors is a motion sensor operable to detect motion of the user.

3. A fall prevention device according to claim 1 which comprises a light apparatus.

4. A fall prevention device according to claim 3 comprising a connection between the sensor or at least one of the sensors and the light apparatus, wherein the light apparatus is operable to generate a signal along the connection when the light apparatus turns on and the sensor is operable to detect the generated signal as the event.

5. A fall prevention device according to claim 1 wherein the notification unit comprises a light source operable to output light as part of the fall prevention warning.

6. A fall prevention device according to claim 1 wherein the notification unit comprises a transmitter operable to output a signal to turn on a light source as part of the fall prevention warning.

7. A fall prevention device according to claim 6, when dependent upon claim 3, wherein the light apparatus comprises a receiver operable to receive the outputted signal from the transmitter and a switch operable to turn the light apparatus on in response to the receiver receiving the outputted signal.

8. A fall prevention device according to claim 1 wherein the notification unit comprises a speaker operable to output audio as part of the fall prevention warning.

9. A fall prevention device according to claim 8 wherein the speaker is operable to output a verbal communication as part of the fall prevention warning.

10. A fall prevention device according to claim 9 comprising a microphone operable to record audio for use as part of the fall prevention warning.

11. A fall prevention device according to any of claims 8 to 10 comprising a receiver operable to receive audio recordings, for use as part of the fall prevention warning, from an exterior source.

12. A fall prevention device according to claim 1 wherein the notification unit comprises an induction loop operable to output instructions to a hearing aid, instructing a hearing aid to output audio, as part of the fall prevention warning.

13. A fall prevention device according to claim 1 wherein the notification unit is operable to stop outputting the fall prevention warning in response to the sensor no longer detecting the event.

14. A fall prevention device according to claim 1 comprising a controller operable to monitor the time of day and control the notification unit so that it can only output the fall prevention warning to the user in response to the detection at certain times of the day.

15. A fall prevention device according to claim 1 wherein the notification unit is operable to choose one of a plurality of fall prevention warnings to output based on a set of criteria.

16. A fall prevention device according to claim 1 comprising an input unit and a processor, the input unit operable to receive a calibration input from a user and the processor operable, in response to the input unit receiving the calibration input, to record the next change detected by the sensor or at least one of the sensors and set the detected change as the set threshold or respective set threshold.

17. The fall prevention device of claim 1, wherein the fall prevention device comprises a body, the or each sensor and notification unit form part of the body and, in use, the body is placed on a bedside next to a user in a bed.

18. A fall prevention device comprising one or more sensors, one or more of the sensors being operable to detect a user is awake while they are still within a bed and a notification unit operable to output a fall prevention warning to the user in response to the detection; wherein at least one of the sensors is a light sensor operable to detect a change in the light intensity of an environment, compare the detected change to a set threshold or respective set threshold for light intensity, and determine whether the detected change indicates the user is awake based on the comparison, and further comprising an input unit and a processor, the input unit operable to receive a calibration input from a user and the processor operable, in response to the input unit receiving the calibration input, to record the next change detected by the sensor or at least one of the sensors and set the detected change as the set threshold or respective set threshold.

* * * * *